(12) United States Patent
Britten et al.

(10) Patent No.: US 6,878,335 B2
(45) Date of Patent: Apr. 12, 2005

(54) PROCESS OF MANUFACTURING A BREATHING BAG AND BREATHING BAG MANUFACTURED BY SUCH PROCESS

(75) Inventors: Jack H. Britten, Blairstown, NJ (US); Mark E. Woelfel, Stockholm, NJ (US); Richard Kennedy, Mine Hill, NJ (US)

(73) Assignee: Vital Signs, Inc., Totawa, NJ (US)

( * ) Notice: Subject to any disclaimer, the term of this patent is extended or adjusted under 35 U.S.C. 154(b) by 215 days.

(21) Appl. No.: 10/176,906

(22) Filed: Jun. 21, 2002

(65) Prior Publication Data

US 2003/0234020 A1 Dec. 25, 2003

(51) Int. Cl.[7] .......................... B29C 49/04; B29C 49/54
(52) U.S. Cl. ...................... 264/527; 264/531; 264/340; 264/571
(58) Field of Search ................................ 264/527, 531, 264/540, 571; 128/205.13

(56) References Cited

U.S. PATENT DOCUMENTS 5,391,248 A * 2/1995 Brain ......................... 156/242
6,290,094 B1 * 9/2001 Arnold et al. ............... 220/839
6,495,089 B1 * 12/2002 Crider ........................ 264/531

* cited by examiner

Primary Examiner—Suzanne E. McDowell
(74) Attorney, Agent, or Firm—R. Gale Rhodes, Jr.

(57) ABSTRACT

Process for manufacturing a breathing bag including a connector portion and a distensible portion including the steps of providing moldable material, forming a portion of the moldable material into the connector portion of the breathing bag and forming another portion of the moldable material into the distensible portion of the breathing bag. The moldable material may be provided by extruding a parison of thermoplastic material; the connector portion of the breathing bag may be formed by compression molding and the distensible portion of the breathing bag may be formed by blow molding or blow and vacuum molding; such distensible portion and connector portions are formed or molded integrally. A breathing bag made by such process.

12 Claims, 8 Drawing Sheets

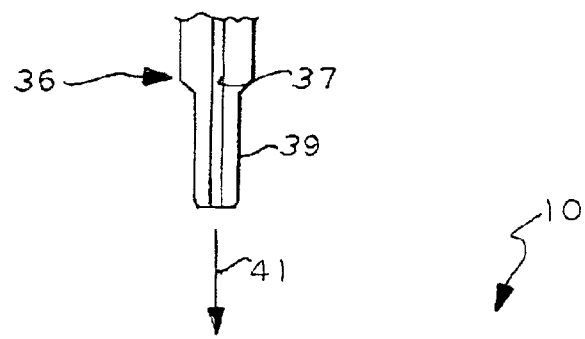
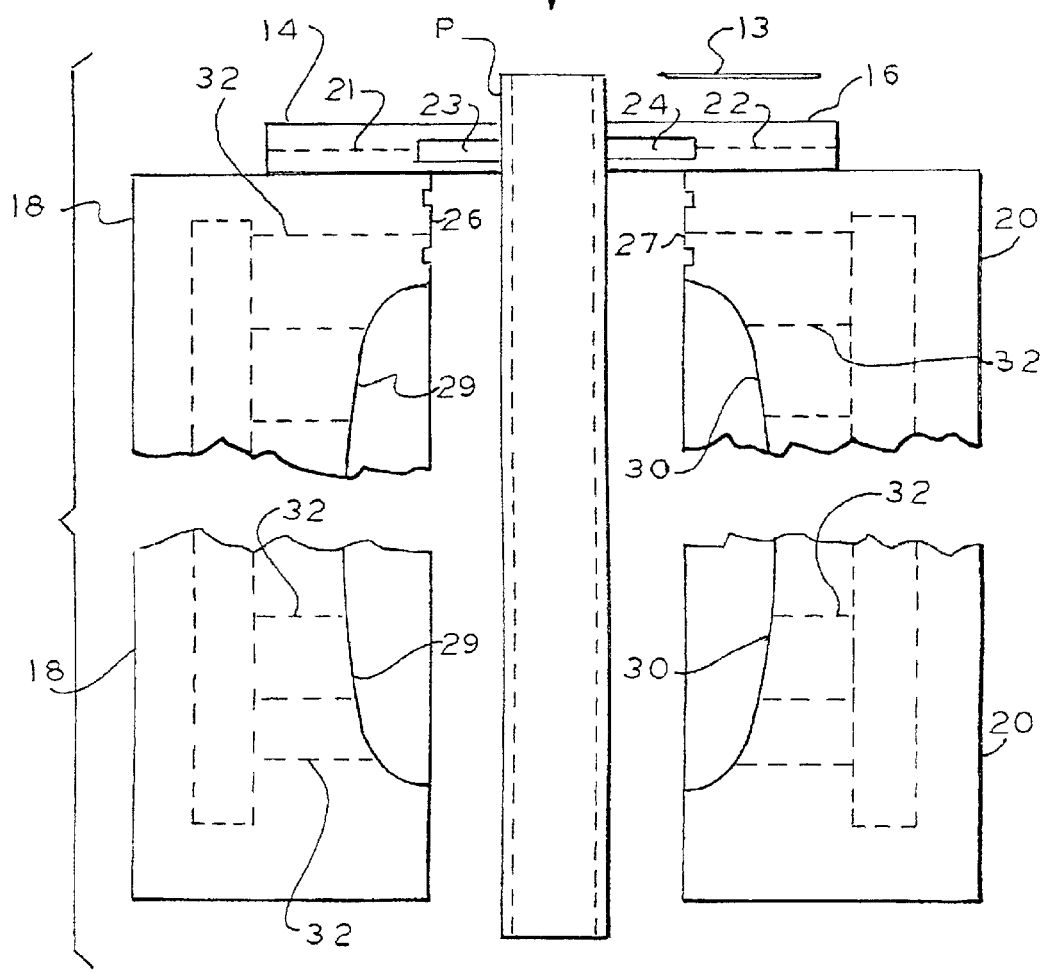

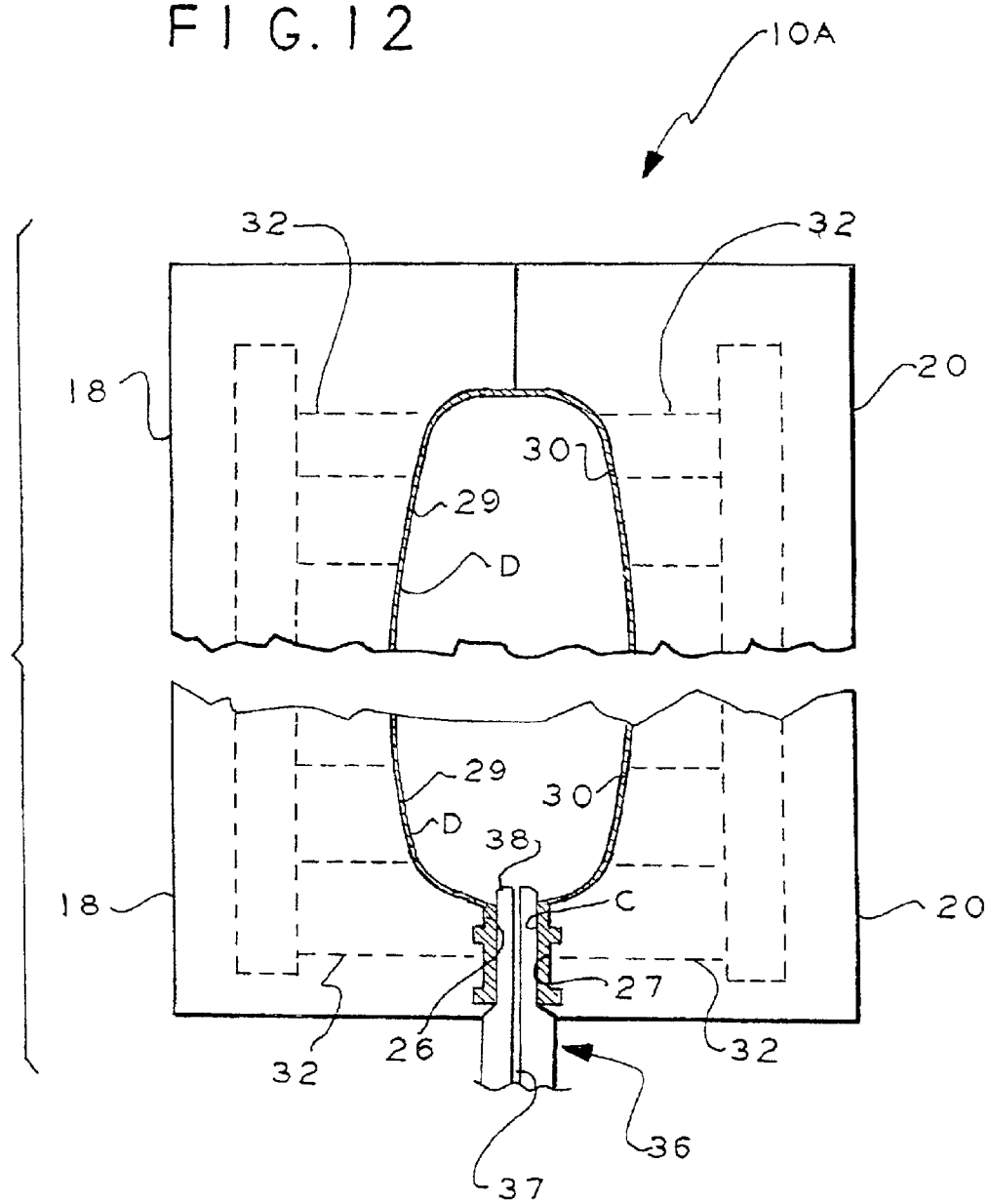

PROCESS OF MANUFACTURING A BREATHING BAG AND BREATHING BAG MANUFACTURED BY SUCH PROCESS

BACKGROUND OF THE INVENTION

This invention relates to a process of manufacturing a breathing bag and to a breathing bag manufactured by such process.

Breathing bags are well known to the medical arts for delivering, or assisting in delivering, gas to a patient such as anesthesia gas or a breathing gas such as oxygen or oxygen-enriched air. Typical prior art breathing bags are illustrated diagrammatically in FIGS. 1A and 1B, FIGS. 2A and 2B, FIGS. 3A, 3B and 3C and FIGS. 4A, 4B and 4C.

Typically, in the prior art, such breathing bags are made by the dipping process much like the process used for producing a candle. A form is made in the shape of the breathing bag desired and the form is dipped repeatedly into a fluid suitable for producing a breathing bag such as, for example, a latex or non-latex fluid. Such process is typically slow, unwantedly expensive and lends itself to imperfections.

Further, the typical prior art breathing bag is made by the aforenoted dipping process and has a relatively thin wall thickness such that the connector portion is insufficiently stiff or rigid to connect, for example, to a standard 22 mm tapered male fitting or a non-tapered tubular or hollow cylindrical fitting. More particularly and referring to FIGS. 5 and 5A, these FIGS. show a typical prior art breathing bag made by the above-noted dipping process and each breathing bag includes a distensible portion 2 and a neck portion 4. Having been made by the above-noted dipping process, the distensible portions 2 and the neck portions 4 are typically 0.010–0.015 inch thick. Such thickness means that the neck portions 4 are insufficiently stiff or rigid to be connected directly to one of the above-noted male fittings. Hence, as is further known to the art, these prior art breathing bags made by the dipping process require the addition of a separate cylindrical bushing such as the bushings 5 and 6 shown respectively in FIGS. 5 and 5A to be inserted into the neck portion to provide the required stiffness or rigidity to permit these breathing bags to be connected to the above-noted male fittings. Typically, such bushings 5 and 6 are made from polyvinyl chloride and have a wall thickness of about 0.125 inch. Although such bushings 5 and 6 are sufficiently rigid or stiff to permit the breathing bags to be connected to one of the above-noted fittings, such bushings are still sufficiently soft to permit the bushings to slidably or wedgedly engage the above-noted male fittings. As will be noted from FIG. 5, the bushing 5 has an inwardly tapered internal wall for being fitted to a tapered male fitting in a sliding or wedged air-tight engagement, and the bushing 6 in FIG. 5A has a straight or cylindrical internal wall for air-tight sliding or wedged engagement with a tubular or cylindrical fitting. Further, as will be understood from FIG. 5A, to retain the bushings 5 and 6 in the neck portion 4 of these breathing bags, an additional element is included such as the surrounding retaining ring or band 7 shown in FIG. 5A which surrounds the bag neck portion 4 sufficiently tightly so as to retain the bushing 6 in the neck portion of the breathing bag. As is further known to the art, the requirement of these additional bushings, the retaining bands, and the manufacturing steps required to insert and retain the bushings in the breathing bags further add unwanted cost and expense to the manufacture of the typical prior art breathing bag.

Accordingly, there is a need in the breathing bag art for a new and improved process for manufacturing a breathing bag and for a new and improved breathing bag manufactured by such process. Still further, there is a need in the breathing bag art for a new and improved process of manufacturing which produces a neck portion formed integrally with the distensible portion and which neck portion is sufficiently stiff or rigid to permit it to connect the breathing bag directly to a male fitting of the types noted above.

SUMMARY OF THE INVENTION

Process for manufacturing a breathing bag including a connector portion and a distensible portion including the steps of providing moldable material, forming a portion of the moldable material into the connector portion of the breathing bag and forming another portion of the moldable material into the distensible portion of the breathing bag. The moldable material may be provided by extruding a parison of thermoplastic material; the connector portion of the breathing bag may be formed by compression molding and the distensible portion of the breathing bag may be formed by blow molding or blow and vacuum molding; such distensible and connector portions are formed or molded integrally. A breathing bag made by such process.

DESCRIPTION OF THE DRAWINGS

FIGS. 7–9 illustrate, diagrammatically, the process of the present invention for manufacturing a breathing bag and also illustrate, diagrammatically, apparatus suitable for practicing such process;

FIG. 8A is a diagrammatical illustration of a portion of a combination blowing and forming member which may be included in the apparatus for practicing the process of the present invention; and FIGS. 10–12 illustrate, diagrammatically, a second embodiment of the process of the present invention for manufacturing a breathing bag and further illustrate, diagrammatically, apparatus suitable for practicing such process.

It will be generally understood that the opposite sides of the bags shown in FIGS. 1B, 2B, 3B and 4B are also provided with flutes in the same manner as the sides of these bags shown in these FIGS.

DESCRIPTION OF THE PREFERRED EMBODIMENTS

Figure 6:
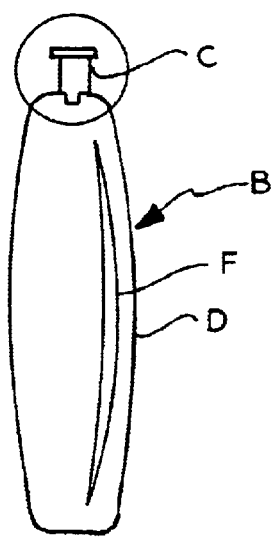
FIG. 6 is a side elevational view of a breathing bag embodying the present invention and made by the process of the present invention.
Figure 6A:
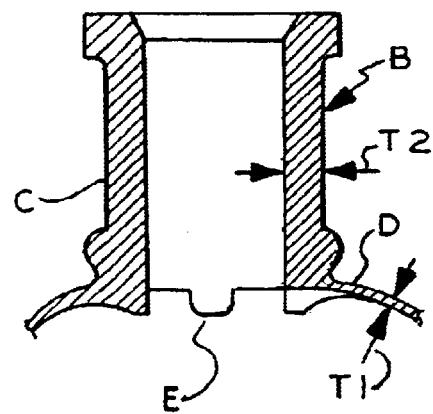
FIG. 6A is an enlarged view in cross-section of the encircled portion of FIG. 6.

A breathing bag embodying the present invention is illustrated diagrammatically in FIGS. 6 and 6A and indicated by alphabetical designation B. Breathing bag B includes a connector portion C and a distensible portion D. The connector portion C is typically sized to connect directly to an ISO 22 mm male fitting and the distensible bag D expands and contracts in the process of delivering, or assisting in delivering, gas to the patient as noted above. As will be better understood from FIG. 6A, the connector portion C has a greater thickness than the thickness of the distensible portion D; the greater thickness of the connector portion C provides it with the strength or rigidity to serve its above-noted connector function. For illustration the thickness of the connector portion C has been exaggerated with respect to the thickness of the distensible portion D in FIG. 6A. In one embodiment, the distensible portion D had a thickness T1 of about 0.015–0.020 inch and the neck portion C had a thickness T2 of about 0.125 inch. In accordance with the teaching of the present invention, the neck portion C is provided with sufficient rigidity or stiffness to permit such neck portion C to connect the breathing bag B, FIGS. 6 and 6A, directly to the above-noted male fittings, and yet be sufficiently flexible or soft that it can engage such fittings in a sliding or wedged air-tight engagement. Anti-occlusion ridges E (FIG. 6A) may be molded in to maintain a positive airway.

Figure 7:
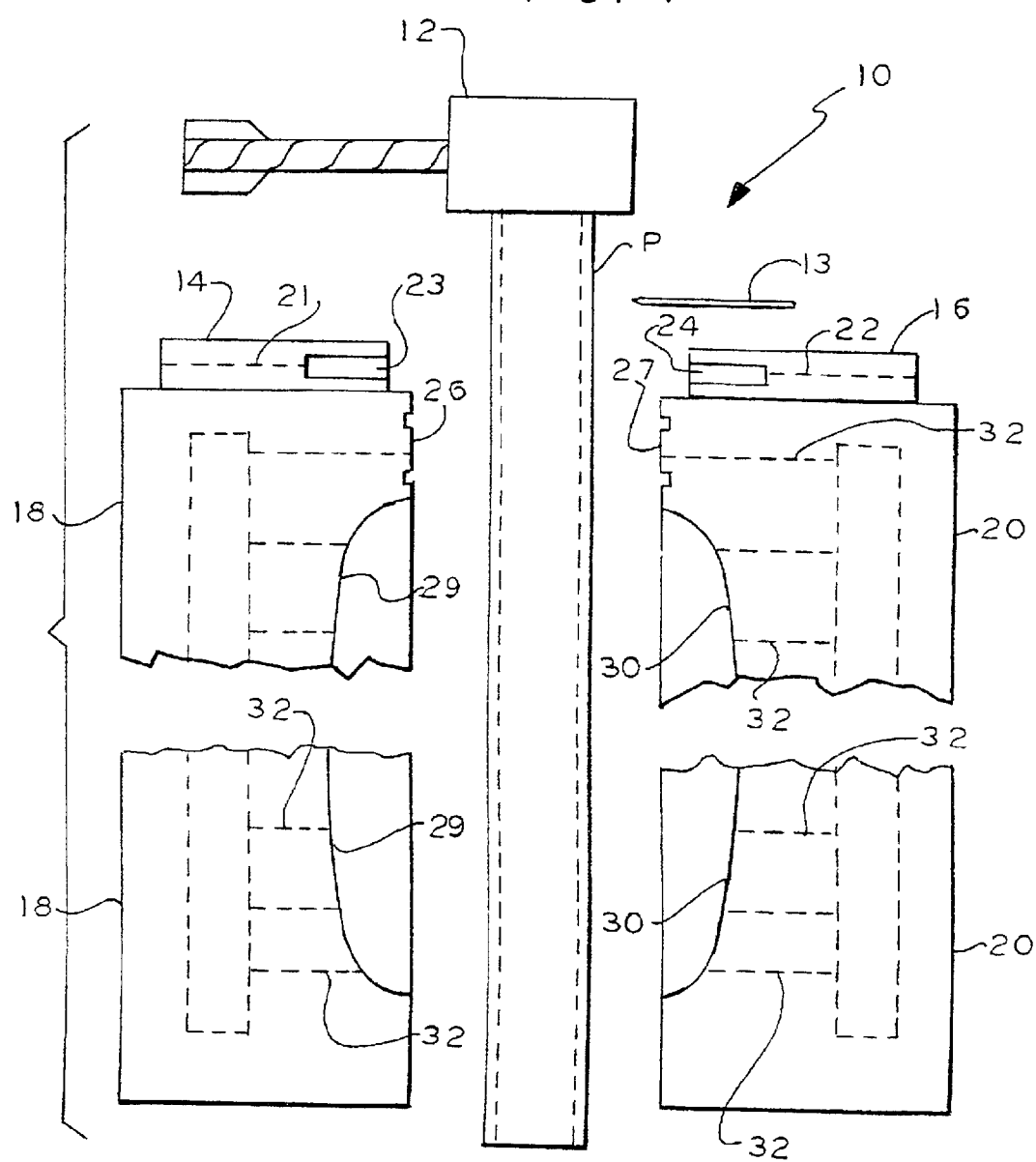
Figure 9:
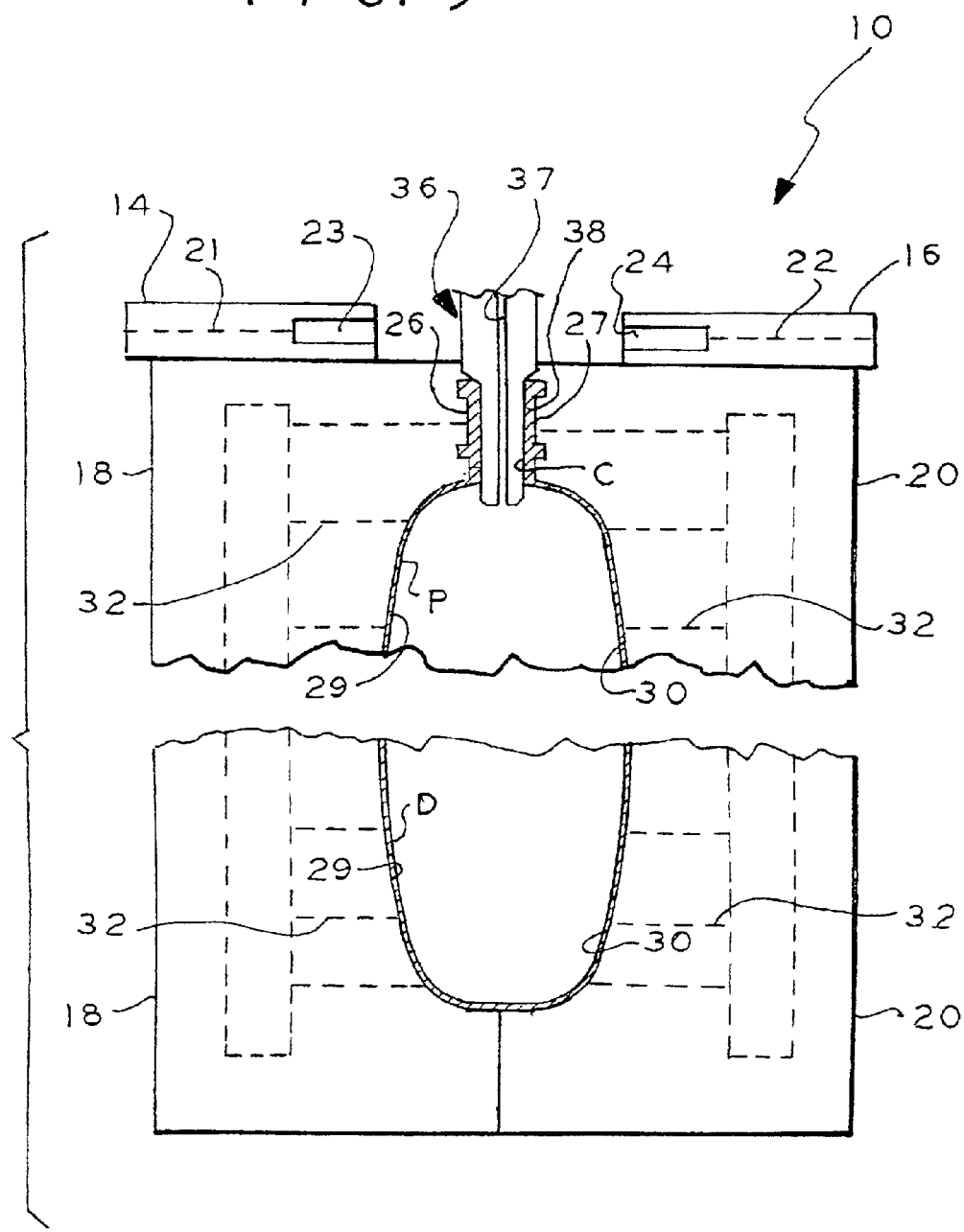

The process for manufacturing a breathing bag according to the present invention is illustrated diagrammatically in FIGS. 7–9. Such process will be described by way of example with respect to a process for manufacturing the breathing bag B illustrated in FIGS. 6, and 6A. Also illustrated diagrammatically in FIGS. 7–9 are apparatus indicated by general numerical designation 10 suitable for practicing such process. Apparatus 10 may include an extruder 12 for extruding a hollow tubular parison of thermoplastic material suitable for making the breathing bag B. As known to the art, a parison is a hollow tubular length of relatively molten, or semi-molten, thermoplastic material. The apparatus 10 further includes a hot cutting knife 13 for cutting the parison and a pair of opposed main molds 18 and 20. The main molds are mounted for sliding reciprocal movement toward and away from each other in the manner known to the art.

The main molds 18 and 20 are provided with connector forming portions 26 and 27 for forming the exterior of the connector portion C of the breathing bag B (FIGS. 5, 6 and 6A) and are further provided with opposed centrally formed mold cavities 29 and 30 for forming the distensible portion D of the breathing bag B. The forming portions 26 and 27 of the main molds 18 and 20 are complementary in shape to the exterior of the connector portion C of the breathing bag B of FIGS. 5, 6 and 6A and the mold cavities 29 and 30 are complementary in shape to the distensible portion D of the breathing bag B.

Referring to FIG. 8A, the apparatus 10 may further include a combination blowing and forming member indicated by general numerical designation 36. The member 36 is provided with a centrally formed passageway 37 through which pressurized air is blown into the interior of the parison to expand and force a portion of the parison wall into the mold cavities 29 and 30 (FIG. 9) and is further provided with an external surface 38 for forming the internal surface, or hollow interior portion of the connector portion C of the breathing bag B (FIG. 6A). It will be understood that such external surface 38 is shaped complementarily to the external shape of the male fitting to which the connector portion C, FIG. 6A, of the breathing bag B will engage in a sliding or wedged air-tight fit. Accordingly, such external surface 38 of the combination blowing and forming member 36 may be provided with a shape so as to provide the connector portion C, FIG. 6A, or the hollow interior portion thereof, with a tapered shape or a non-tapered straight or cylindrical shape for receiving either a tapered male fitting or a non-tapered male fitting in a sliding or wedged air-tight engagement.

The process for manufacturing a breathing bag in accordance with the present invention, and with regard to the breathing bag B of FIGS. 5 and 6 by way of example, will now be described in reference to FIGS. 7–9. The parison P, FIG. 7, is extruded downwardly by the extruder 12 between the pair of open main molds 18 and 20. The hot cutting knife 13 cuts off the upper portion of the parison P and the extruder 12 (FIG. 7) is suitably indexed away. The combination blowing and forming member 36 is then suitably indexed into position over the open upper portion of the parison P, FIG. 8, and is inserted into the upper portion of the parison P as indicated by the arrow 41 in FIG. 8A.

As further illustrated in FIG. 9, the main molds 18 and 19 are advanced toward an engagement with each other to cause the connector forming portions 26 and 27 and the outer surface 38 of the combination blowing and forming member 36 to compression form or mold therebetween the upper portion of the parison P into the connector portion C of the breathing bag B (FIG. 6). Pressurized air is blown into the interior of the parison P through the passageway 37 formed in the combination blowing and forming member 36 to expand and force the lower portion of the parison P into engagement with the surfaces defining the mold cavities 29 and 30 to thereby blow mold the distensible portion D of the breathing bag B (FIG. 6).

The combination blowing and forming member 36 is withdrawn and the main molds 18 and 20 are then retracted or opened and the now formed breathing bag B, of FIG. 6, has been manufactured in accordance with the manufacturing process of the present invention.

It will be understood in accordance with the further teachings of the present invention that if desired or required, the blow-molding step may be accompanied by a vacuum assisted molding step to further enhance the molding of the distensible portion D of the breathing bag B of FIG. 6. In such event, this additional method step will be practiced by providing the main molds 18 and 20, FIGS. 8–9, with vacuum lines or channels 22 for applying vacuum to the lower portion of the parison P (FIG. 9) to assist in expanding and forcing such portion of the parison P into the mold cavities 29 and 30.

Referring again to FIG. 6A, and as noted above, the connector portion C of the breathing bag B is thicker than the thickness of the distensible portion D. It has been found that it is further desirable to provide additional parison material in the breathing bag manufacturing process to enhance the forming of the connector portion D of the breathing bag B so as to have a greater thickness than the distensible portion D of the breathing bag. Accordingly, and referring now to FIGS. 10–12, an alternate process for manufacturing a breathing bag according with the present invention is illustrated diagrammatically and apparatus suitable for practicing this alternate process is also illustrated diagrammatically in these figures and indicated by general numerical designation 10A. It will be understood that the components comprising the apparatus 10A in FIGS. 10–12 which are the same as the components comprising the apparatus 10 in FIGS. 7–9 are given the same numerical designations in FIGS. 10–12 and will be understood to perform the same functions.

Figure 11:
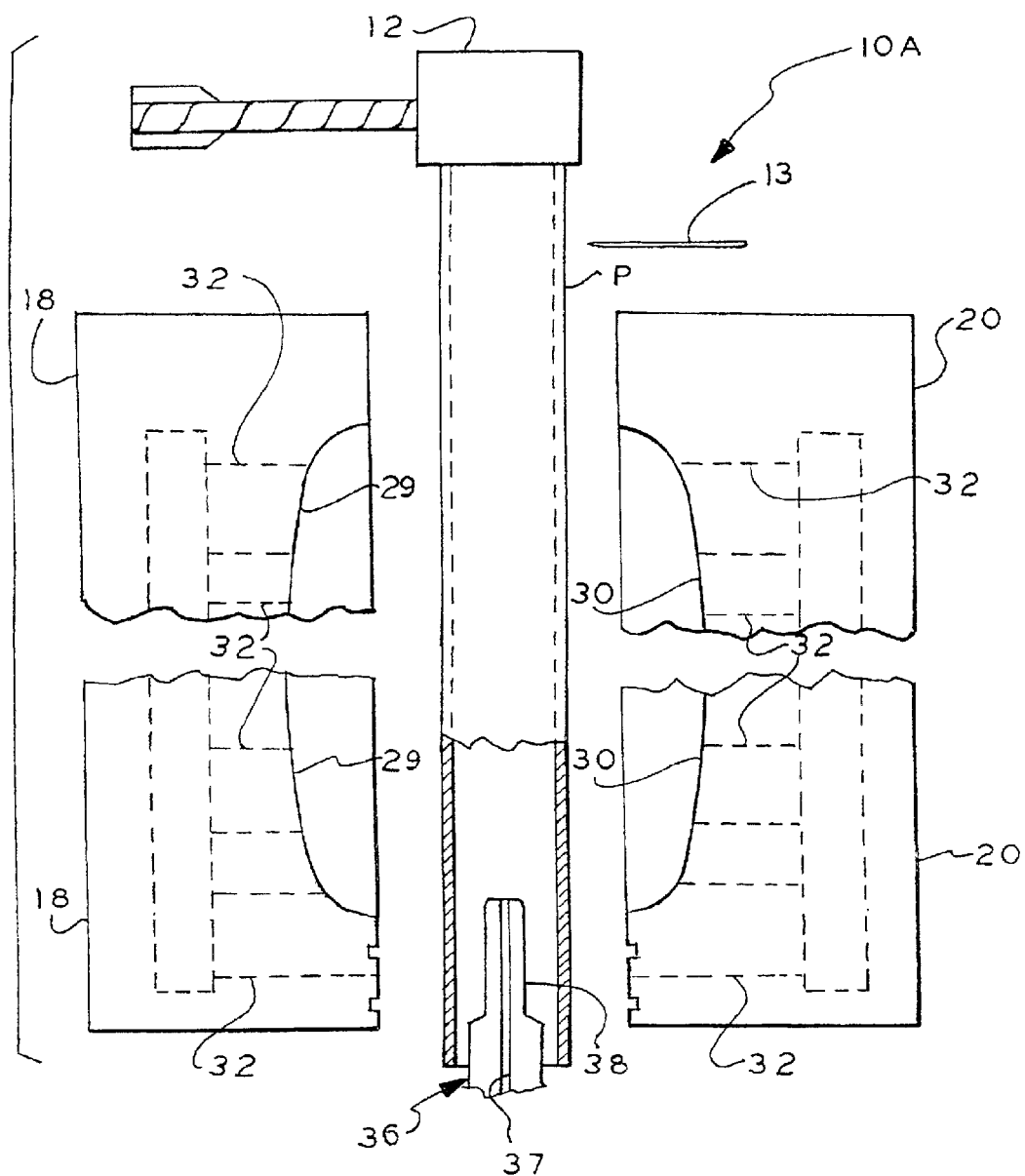

It has been discovered that upon the parison P, FIG. 11, being extruded vertically downwardly, that at least the lower portion of the parison P increases in thickness with respect to the upper portion of the parison under the influence of gravity. It has been further discovered that this thickening of the lower portion of the parison P can be utilized advantageously in forming the connector portion C of the breathing bag B of FIGS. 6 and 6A. The thickening of the lower portion of the parison P under the influence of gravity is illustrated diagrammatically in FIG. 11 by the cross-sectioned lower portion of such parison.

Figure 10:
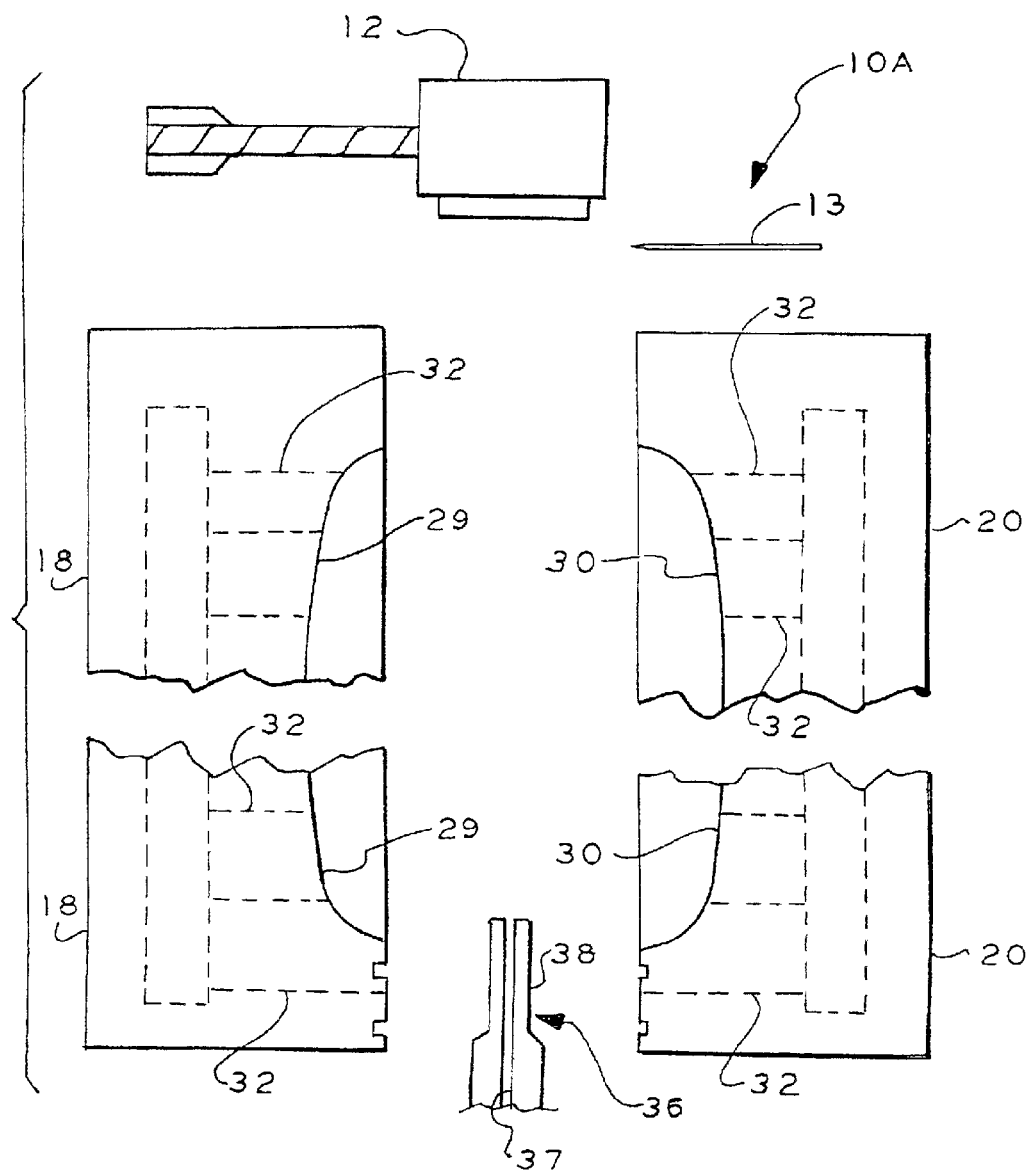

It will be generally understood, that the primary difference between the alternate embodiment process of FIGS. 10–12 and the foregoing described process of FIGS. 7–9 is that the breathing bag in FIGS. 10–12 is formed upside down with respect to the orientation of the breathing bag formed by the process illustrated diagrammatically in FIGS. 7–9. Accordingly, and referring to FIG. 11, the parison P of hollow cylindrical suitable thermoplastic material is extruded vertically downwardly between the open main molds 18 and 20 and the lower portion of such parison is extruded downwardly by the extruder 12 over the combination blowing and forming member 36 and the lower portion of the parison P is allowed to increase in thickness under the influence of gravity. The main molds 18 and 20, FIG. 12, are advanced into engagement with each other, the cutting knife 13 cuts the parison P, the extruder 12 is suitably indexed out of the way, and pressurized air is blown into the interior of the upper portion of the parison P through the combination blowing and forming member 36 and, if desired or required, vacuum is drawn against the exterior of the upper portion of the parison P through the vacuum lines 32 to force the upper portion of the parison P into the mold cavities 29 and 30 and to expand such upper portion of the parison P to form the distensible portion D of the breathing bag B of FIGS. 5 and 6 by pressure molding or by pressure and vacuum molding. The connector forming portions 26 and 27 of the main molds 18 and 19 and the outer forming surface 38 of the combination blowing and forming member 36 engage the lower portion of increased thickness of the parison P and compression mold or form therebetween the connector portion C of the breathing bag B as illustrated diagrammatically in FIG. 12.

Figure 1A:
FIGS. 1A and B illustrate, respectively, a side elevational view of a double fluted standard prior art breathing bag with a nipple.
Figure 1B:
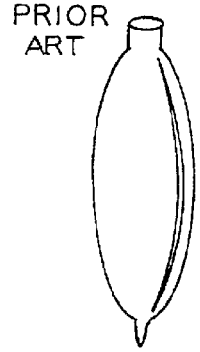
FIG. 1B shows the flutes and is rotated approximately 45° with respect to FIG. 1A.
Figure 2A:
FIGS. 2A and 2B show a bag similar to that shown in FIGS. 1A and 1B except the prior art bag in FIGS. 2A and 2B does not include the nipple.
Figure 2B:
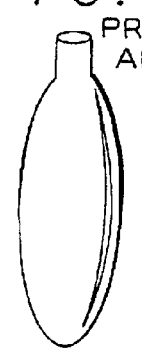
Figure 3A:
FIG. 3A is a side elevational view of a double fluted prior art paddle bag with a nipple and FIG. 3B shows the bag of FIG. 3A rotated approximately 45° and illustrates the double flute.
Figure 3B:
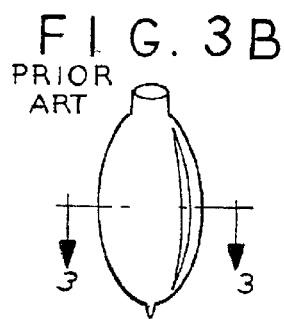
Figure 4A:
FIG. 4A is a side elevational view of a standard prior art breathing bag with triple flutes which flutes are shown in FIG. 4B which FIG. is rotated approximately 45° with respect to FIG. 4A, this bag also is provided with a nipple.
Figure 4B:
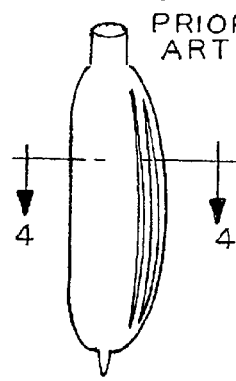
FIG. 4C is a diagrammatical cross-sectional view taken generally along the line 4—4 in FIG. 4D in the direction of the arrows and shows more clearly the triple fluting.
Figure 3C:
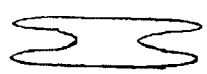
FIG. 3C is a cross-sectional view taken generally along the line 3—3 in FIG. 2D in the direction of the arrows and illustrates more clearly the double fluting.
Figure 4C:
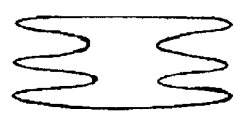
Figure 5:
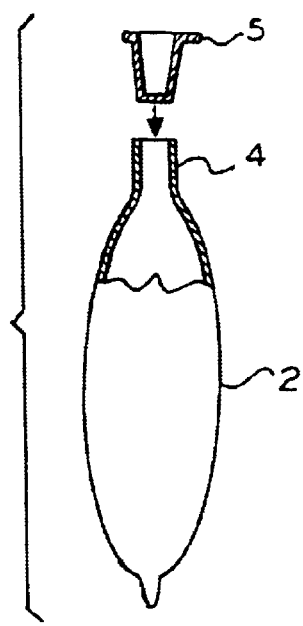
FIGS. 5 and 5A illustrate, in perspective, a still further breathing bag known to the art.
Figure 5A:

Thereafter, the main molds are retracted into the open position shown in FIGS. 10 and 11 and the combination blowing and forming member 36 is withdrawn and suitably indexed away and the breathing bag B of FIGS. 5 and 6 is removed.

It has been found, by way of example and not by way of limitation, that a thermoplastic material from QST Inc., Ateknor Apex Co., 300 Industrial Park Road, St. Albans, Vt., sold under the trademark MONOPRENE, is suitable for use in the processes of the present invention for manufacturing a breathing bag.

Referring again to the parison P, FIGS. 7, 8 and 11, it will be understood that the tubular parison P may be circular in cross-section, rectangular in cross-section, or of other cross-sectional shapes to enhance the manufacture of the breathing bag in accordance with the processes of the present invention.

It will be understood that many variations and modifications may be made in the present invention without departing from the spirit and scope thereof.

What is claimed is:

1. Process for manufacturing a breathing bag including a connector portion and a distensible portion, comprising the steps of:

providing formable material; and forming a first portion of said formable material into the connector portion of the breathing bag and to have a first wall thickness sufficiently thick to permit said connector portion to be connected directly to a male fitting, and forming a second portion of said formable material into the distensible portion of the breathing bag and to have a second wall thickness sufficiently thin to permit said distensible portion to expand and contract in delivering or assisting in delivering gas to a patient, said second wall thickness being smaller than said first wall thickness.

2. Process for manufacturing a breathing bag including a connector portion and a distensible portion, comprising the steps of:

providing moldable material; and pressure molding a first portion of said moldable material into the connector portion of the breathing bag and to have a first wall thickness sufficiently thick to permit said connector portion to be connected directly to a male fitting, and blow and vacuum molding a second portion of said moldable material into the distensible portion of the breathing bag and to have a second wall thickness sufficiently thin to permit said distensible portion to expand and contract in delivering or assisting in delivering gas to a patient, said second wall thickness being smaller than said first wall thickness.

3. Process for forming a breathing bag including a connector portion and a distensible portion; comprising the steps of:

extruding a tubular parison of thermoplastic material; and molding a first portion of said parison into the connector portion of the breathing bag and to have a first wall thickness sufficiently thick to permit said connector portion to be connected directly to a male fitting, and molding a second portion of said parison into the distensible portion of the breathing bag and to have a second wall thickness sufficiently thin to permit said distensible portion to expand and contract in delivering or assisting in delivering gas to a patient, said second wall thickness being smaller than said first wall thickness.

4. Process for manufacturing a breathing bag including a connector portion and a distensible portion, comprising the steps of:

extruding a tubular parison of thermoplastic material; and forming a first portion of said parison into said connector portion of said breathing bag by compression molding and forming a second portion of said parison into said distensible portion of said breathing bag by applying pressurized air to the interior of said second portion of said parison and by applying vacuum to the exterior of said second portion of said parison to expand and form said second portion of said parison into the distensible portion of the breathing bag by blow and vacuum molding.

5. Process for manufacturing a breathing bag including a connector portion and a distensible portion, comprising steps of:
  extruding a tubular parison of thermoplastic material between a pair of open molds including opposed forming portions complementary in shape to the exterior of the connector portion of the breathing bag and including a pair of opposed mold cavities complementary in shape to the distensible portion of the breathing bag;
  inserting a combination blowing and forming member into a first portion of said parison, said forming member including an outer surface complementary in shape to the interior shape of the connector portion; and
  closing said molds to cause said forming portions of said molds to engage a first portion of said parison to form said first portion of parison into the connector portion of the breathing bag between said forming portions of said molds and said outer surface of said combination blowing and forming member and applying pressurized air through said combination blowing and forming member into the interior of a second portion of said parison and applying vacuum to the outer surface of said second portion of said parison to force said second portion of said parison into engagement with said mold cavities to form said second portion of said parison into said distensible portion of the breathing bag.

6. Process for manufacturing a breathing bag including a connector portion and a distensible portion, comprising steps of:
  extruding a tubular parison of thermoplastic material vertically downwardly and allowing the lower portion of said parison to increase in thickness under the influence of gravity;
  compression molding the lower portion of said parison into the connector portion of the breathing bag and expanding the upper portion of said parison by blow and vacuum molding to form the distensible portion of the breathing bag.

7. Process for manufacturing a breathing bag including a connector portion and a distensible portion, comprising steps of:
  extruding a tubular parison of thermoplastic material vertically downwardly to cause the upper portion of said parison to reside between a pair of opposed open molds provided with opposed cavities complementary in shape to the distensible portion of the breathing bag and to cause the lower portion of said parison to pass over a combination blowing and forming member provided with an exterior complementary in shape to the interior of the connector portion of the breathing bag, and said molds further provided with opposed forming members complementary in shape to the exterior of the connector portion of the breathing bag;
  allowing said lower portion of said parison to increase in thickness under the influence of gravity; and
  closing said molds and applying pressurized air through said combination blowing and forming member to the interior of said upper portion of said parison and applying vacuum to the exterior of said upper portion of said parison to expand said upper portion of said parison into said mold cavities to form said upper portion of said parison into the distensible portion of the breathing bag and to cause said forming portions of said molds to engage said lower portion of said parison and force said lower portion of said parison against the exterior of said combination blowing and forming member to compression form said lower portion of said parison into the connector portion of the breathing bag.

8. Process for manufacturing a breathing bag including a connector portion and a distensible portion, comprising the steps of:
  providing moldable material; and
  pressure molding a first portion of said moldable material into the connector portion of the breathing bag and to have a first wall thickness sufficiently thick to permit said connector portion to be connected directly to a male fitting, and blow molding a second portion of said moldable material into the distensible portion of the breathing bag and to have a second wall thickness sufficiently thin to permit said distensible portion to expand and contract in delivering or assisting in delivering gas to a patient, said second wall thickness being smaller than said first wall thickness.

9. Process for manufacturing a breathing bag including a connector portion and a distensible portion, comprising the steps of:
  extruding a tubular parison of thermoplastic material; and
  forming a first portion of said parison into said connector portion of said breathing bag by compression molding and to have a first wall thickness sufficiently thick to permit said connector portion to be connected directly to a male fitting, and forming a second portion of said parison into said distensible portion of said breathing bag by applying pressurized air to the interior of said second portion of said parison to expand and form said second portion of said parison into the distensible portion of the breathing bag by blow molding and to have a second wall thickness sufficiently thin to permit said distensible portion to expand and contract in delivering or assisting in delivering gas to a patient, said second wall thickness being smaller than said first wall thickness.

10. Process for manufacturing a breathing bag including a connector portion and a distensible portion, comprising steps of:
  extruding a tubular parison of thermoplastic material between a pair of open molds including opposed forming portions complementary in shape to the exterior of the connector portion of the breathing bag and including a pair of opposed mold cavities complementary in shape to the distensible portion of the breathing bag;
  inserting a combination blowing and forming member into a first portion of said parison, said forming member including an outer surface complementary in shape to the interior shape of the connector portion; and
  closing said molds to cause said forming portions of said molds to engage a first portion of said parison to form said first portion of parison into the connector portion of the breathing bag between said forming portions of said molds and said outer surface of said combination blowing and forming member and to have a first wall thickness sufficiently thick to permit said connector portion to be connected directly to a male fitting, and applying pressurized air through said combination blowing and forming member into the interior of a second portion of said parison to force said second portion of said parison into engagement with said mold cavities to form said second portion of said parison into said distensible portion of the breathing bag and to have a second wall thickness sufficiently thin to permit said distensible portion to expand and contract in delivering or assisting in delivering gas to a patient, said second wall thickness being smaller than said first wall thickness.

11. Process for manufacturing a breathing bag including a connector portion and a distensible portion, comprising steps of:

extruding a tubular parison of thermoplastic material vertically downwardly and allowing the lower portion of said parison to increase in thickness under the influence of gravity;

compression molding the lower portion of said parison into the connector portion of the breathing bag and to have a first wall thickness sufficiently thick to permit said connector portion to be connected directly to a male fitting, and expanding the upper portion of said parison by blow molding to form the distensible portion of the breathing bag and to have a second wall thickness sufficiently thin to permit said distensible portion to expand and contract in delivering or assisting in delivering gas to a patient, said second wall thickness being smaller than said first wall thickness.

12. Process for manufacturing a breathing bag including a connector portion and a distensible portion, comprising steps of:

extruding a tubular parison of thermoplastic material vertically downwardly to cause the upper portion of said parison to reside between a pair of opposed open molds provided with opposed cavities complementary in shape to the distensible portion of the breathing bag and to cause the lower portion of said parison to pass over a combination blowing and forming member provided with an exterior complementary in shape to the interior of the connector portion of the breathing bag, and said molds further provided with opposed forming members complementary in shape to the exterior of the connector portion of the breathing bag;

allowing said lower portion of said parison to increase in thickness under the influence of gravity; and closing said molds and applying pressurized air through said combination blowing and forming member to the interior of said upper portion of said parison to expand said upper portion of said parison into said mold cavities to form said upper portion of said parison into the distensible portion of the breathing bag by blow molding and to have a wall thickness sufficiently thin to permit said distensible portion to expand and contract in delivering or assisting in delivering gas to a patient and to have a first wall thickness and to cause said forming portions of said molds to engage said lower portion of said parison and force said lower portion of said parison against the exterior of said combination blowing and forming member to compression mold said lower portion of said parison into the connector portion of the breathing bag and to have a second wall thickness greater than said first wall thickness and to be sufficiently thick to permit said connector portion to be converted directly to a male fitting.

* * * * *